(12) United States Patent
Peuker et al.

(10) Patent No.: US 9,375,292 B2
(45) Date of Patent: Jun. 28, 2016

(54) DEVICE FOR DISPENSING A DENTAL MATERIAL AND METHOD OF DISPENSING

(71) Applicant: 3M INNOVATIVE PROPERTIES COMPANY, Saint Paul, MN (US)

(72) Inventors: Marc Peuker, Schondorf (DE); Alexander Walter, Pürgen (DE); Dieter Poschmann, Starnberg (DE)

( * ) Notice: Subject to any disclaimer, the term of this patent is extended or adjusted under 35 U.S.C. 154(b) by 0 days.

(21) Appl. No.: 14/352,788

(22) PCT Filed: Nov. 9, 2012

(86) PCT No.: PCT/US2012/064276
§ 371 (c)(1),
(2) Date: Apr. 18, 2014

(87) PCT Pub. No.: WO2013/070999
PCT Pub. Date: May 16, 2013

(65) Prior Publication Data
US 2014/0299624 A1    Oct. 9, 2014

(30) Foreign Application Priority Data

Nov. 11, 2011    (EP) ..................................... 11188772

(51) Int. Cl.
*B67D 7/78*    (2010.01)
*A61C 5/06*    (2006.01)
(Continued)

(52) U.S. Cl.
CPC .................. *A61C 5/068* (2013.01); *A61C 5/064* (2013.01); *A61C 5/066* (2013.01); *B65D 75/324* (2013.01); *B65D 75/328* (2013.01); *B65D 81/3266* (2013.01)

(58) Field of Classification Search
CPC .. B65D 77/245; B65D 77/5811; B65D 77/32; B65D 77/36; B65D 77/324; B65D 77/328; B65D 81/3266; A61C 5/06; A61C 5/062; A61C 5/068; A61C 5/064; A61C 5/066; A61C 19/005

USPC ......... 206/229, 219, 221, 63.5; 222/94, 541.6
See application file for complete search history.

(56) References Cited

U.S. PATENT DOCUMENTS 3,635,376 A * 1/1972 Hellstrom ...................... 222/107
3,713,779 A * 1/1973 Sirago et al. .................. 422/413
(Continued)

FOREIGN PATENT DOCUMENTS

| DE | 10009622 | 9/2001 |
|----|----------|--------|
| EP | 1526092 | 4/2005 |
| WO | WO 2005-058182 | 6/2005 |

OTHER PUBLICATIONS

International Search Report for PCT International Application No. PCT/US2012/064276, mailed on Feb. 15, 2013, 5 pages.

*Primary Examiner* — Frederick C Nicolas
*Assistant Examiner* — Randall Gruby
(74) *Attorney, Agent, or Firm* — Nicole J. Einerson

(57) ABSTRACT

A device for dispensing a dental material comprises first compartment and the second compartment formed between interconnected sheet-like layers. The compartments encapsulate a first flowable component and a second flowable component of the dental material. The device has a first seal and a second seal for sealing the first compartment and the second compartment in the device. Each seal is adapted to automatically open in consequence of forcing a component of the dental material toward the seal. The capacity of the first compartment and the second compartment relative to each other is dimensioned such that squeezing out the first component from the first compartment by compressing the first compartment causes the first seal and the second seal to open. The device preferably allows easy and quick activation for use of the stored components.

15 Claims, 1 Drawing Sheet

(51) Int. Cl.
   *B65D 75/32* (2006.01)
   *B65D 81/32* (2006.01)

(56) References Cited

U.S. PATENT DOCUMENTS

| | | | | |
|---|---|---|---|---|
| 3,736,933 | A * | 6/1973 | Szabo | A61M 5/002 206/366 |
| 4,928,852 | A * | 5/1990 | Guiffray | 222/107 |
| 4,952,068 | A * | 8/1990 | Flint | 366/337 |
| 5,215,221 | A * | 6/1993 | Dirksing | A61J 1/067 169/30 |
| 5,660,273 | A * | 8/1997 | Discko, Jr. | 206/229 |
| 6,105,761 | A | 8/2000 | Peuker | |
| 6,264,065 | B1 * | 7/2001 | Jouillat | 222/94 |
| 6,394,803 | B1 * | 5/2002 | Salz et al. | 433/49 |
| 6,503,084 | B2 * | 1/2003 | Evers et al. | 433/226 |
| 6,685,013 | B2 * | 2/2004 | Discko, Jr. | A61C 5/06 206/209 |
| 6,845,883 | B2 * | 1/2005 | Pieri | 222/94 |
| 7,556,147 | B2 * | 7/2009 | Leiner et al. | 206/219 |
| 7,607,534 | B2 * | 10/2009 | Peuker et al. | 206/229 |
| 7,625,114 | B2 * | 12/2009 | Suchan et al. | 366/130 |
| 7,934,864 | B2 * | 5/2011 | Heusser | B01F 5/064 206/222 |
| 8,684,601 | B2 * | 4/2014 | Perell | B65D 75/5855 383/210 |
| 8,806,842 | B1 * | 8/2014 | Penn et al. | 53/453 |
| 9,174,881 | B2 * | 11/2015 | Cimaglio | B65D 81/3266 |
| 9,211,538 | B2 * | 12/2015 | Weber | B01L 3/502738 |
| 2002/0122685 | A1 * | 9/2002 | Lee et al. | 401/118 |
| 2003/0038040 | A1 | 2/2003 | Bertl | |
| 2003/0146117 | A1 * | 8/2003 | Raia et al. | 206/229 |
| 2003/0198918 | A1 * | 10/2003 | Dragan et al. | 433/90 |
| 2004/0029077 | A1 * | 2/2004 | Peuker et al. | 433/217.1 |
| 2004/0029171 | A1 * | 2/2004 | Wagner et al. | 435/7.1 |
| 2004/0065679 | A1 | 4/2004 | Peuker | |
| 2005/0026126 | A1 | 2/2005 | Hageman | |
| 2005/0150904 | A1 * | 7/2005 | Suchan | B65D 75/327 222/94 |
| 2006/0118434 | A1 * | 6/2006 | Leiner | A61C 5/066 206/219 |
| 2006/0131189 | A1 | 6/2006 | Lee | |
| 2007/0119862 | A1 * | 5/2007 | Backes | B65D 1/095 222/94 |
| 2007/0217971 | A1 * | 9/2007 | Michalsky | B65D 81/3266 422/224 |
| 2007/0235369 | A1 * | 10/2007 | Perell | B65D 75/323 206/538 |
| 2008/0230298 | A1 * | 9/2008 | Buch | A61C 5/062 180/311 |
| 2009/0032413 | A1 * | 2/2009 | Huber | B65D 81/3294 206/221 |
| 2011/0027750 | A1 * | 2/2011 | Boehm et al. | 433/89 |
| 2011/0150952 | A1 * | 6/2011 | Simonnet et al. | 424/401 |
| 2013/0284620 | A1 * | 10/2013 | Walter et al. | 206/221 |

* cited by examiner

DEVICE FOR DISPENSING A DENTAL MATERIAL AND METHOD OF DISPENSING

CROSS REFERENCE TO RELATED APPLICATIONS

This application is a national stage filing under 35 U.S.C. 371 of PCT/US2012/064276, filed Nov. 9, 2012, which claims priority to European Application No. 11188772.5, filed Nov. 11, 2011, the disclosures of which are incorporated by reference in their entirety herein.

FIELD OF THE INVENTION

The invention relates to a device for dispensing a dental material, and in particular to a device for dispensing multi-component dental material. The invention further relates to a method of dispensing a dental material from such a device.

BACKGROUND ART

A variety of dental compositions are provided in the form of two or more flowable components that are separately stored, and mixed together only shortly before use. There are different packages for separately storing components of such multi-component compositions. Examples of commonly-used packages for multi-component compositions include dual-chamber cartridges, dual-chamber syringes or dual-chamber blister packages. Such packages are typically designed to provide a readily mixable composition, or to provide the components individually for subsequent mixing. There are also single-use packages for providing suitable amounts of composition for a single treatment.

For example U.S. Pat. No. 6,105,761 discloses a device for storing and dispensing preferably flowable substances. The device preferably includes a container formed by two sheets that are interconnected by heat sealing. The sheets preferably form a compartment for receiving a component, which may be a liquid, and a pocket for receiving a brush. In the area between the compartment and the pocket, the connection between the sheets includes a pre-defined break zone which can be released by pressure exerted on the compartment, to force the liquid from the compartment into the pocket and wet the tip of the brush disposed therein.

DE 100 09 622 discloses a device for storing and dispensing preferably flowable substances. The device preferably includes a container formed by two sheets, interconnected by heat sealing and cooperating to form a compartment for receiving a substance and a pocket for receiving a brush. The device is preferably designed to allow the substance stored in the compartment to be forced in a pocket and from there onto a film sheet where it can be mixed.

US 2006/0131189 discloses a packaging article having chambers preferably defined by sealed connections between films. The device may have one or more receiving chambers which can receive the components that may be stored in the chambers. The receiving chambers are preferably accessible through passageways that extend from the exterior of the device into the receiving chambers. Brushes may be pushed through the passageways for picking up components from the receiving chambers.

There is still a desire for a package that can be used to provide multi-component compositions for different applications. In particular, suitable packages for providing relatively small amounts of a composition are desirable. It is also desirable to provide a package which is easy to use and which helps minimizing the time to prepare a multi-component composition for use. Moreover, there is a need for packages that can be used in health care fields such as in dentistry, with its associated hygiene and infection control requirements. There is also a general need for packages that are relatively inexpensive to manufacture and use.

SUMMARY OF THE INVENTION

In one aspect the invention relates to a device for dispensing a dental material. The device comprises:
- a first compartment and a second compartment formed between interconnected sheet-like layers,
- the first compartment at an inactivated stage encapsulating a first flowable component of the dental material;
- the second compartment at an inactivated stage encapsulating a second flowable component of the dental material;
- a reservoir for holding at least parts of the first component and the second component at an activated stage, preferably having a capacity to jointly hold at least part of the first component and essentially all of the second component at an activated stage;
- a dispensing outlet which opens the reservoir;
- a first seal openably sealing the first compartment and the second compartment at the inactivated stage from each other;
- a second seal openably sealing the second compartment and the reservoir at the inactivated stage from each other;
- each of the first seal and the second seal being formed by the layers in a non-permanent sealing area in which the layers are interconnected such that they are disconnectable in consequence of forcing a component of the dental material between the layers; and
- wherein the capacity of the first compartment and second compartment relative to each other is dimensioned such that squeezing out the first component from the first compartment by compressing the first compartment causes the first seal and the second seal to open.

The invention may be advantageous for providing two- or multi-component materials in single-use quantities. The invention may further allow for rapidly providing an amount of two-component material in a single activation step. Accordingly the device of the invention may help minimizing the number of handling steps to be taken to activate the device and thus may be convenient to use. This may further help minimizing the time needed to prepare a dental material. Further, with the invention a device may be provided which allows storage of the material over a relatively long time. The invention further may provide for a device that is relatively inexpensive.

For the purpose of this specification in the activated stage of the first compartment preferably the first seal is open such that the first flowable component can flow out of the first compartment, whereas in the inactivated stage of the first compartment preferably the first seal is closed such that the first flowable component is encapsulated or sealed within the first compartment. Further in the activated stage of the second compartment preferably the second seal is open such that the second flowable component can flow out of the second compartment, whereas in the inactivated stage of the second compartment preferably the first seal and the second seal are closed such that the second flowable component is encapsulated or sealed within the second compartment. Further in the activated stage of the device preferably both the first seal and the second seal are open. Preferably in the activated stage of the first compartment the first component is displaced, for example a majority or substantially all of the first component is displaced, from the first compartment. Accordingly in the activated stage of the first compartment at least part of the first component is preferably transferred toward the second compartment and thus received within the second compartment. To activate the first compartment, in particular to cause the first compartment to change from the inactivated stage into the activated stage, the compartment may be compressed. Preferably in the activated stage of the second compartment the content in the second compartment, for example at least part of the first component and the second component, is displaced, for example a majority or substantially all of the content is displaced, from the second compartment. The second compartment may activate, in particular may change from the inactivated stage into the activated stage, in consequence of the activation of the first compartment. In the activated stage of the second compartment at least part of the content in the second compartment may be transferred toward the reservoir and thus received within the reservoir. The second compartment may be additionally compressed, for example after activation, to transfer further of the content into the reservoir. However in the alternative the second compartment may be generally incompressible or may be compressible at relatively high forces only. This may be achieved by a reinforcement of the bulge for the second component, for example by insertion of a dome shaped plastic or metal piece into the bulge. Further the resistance of the bulge against being compressed may be maximized by maximizing the depth and minimizing the size laterally to the depth of the bulge. This may help ensuring a desired mixing ratio of the first component and the second component relative to each other.

In one embodiment the device has a permanent sealing area in which the interconnection between the layers is of greater bond strength than in the non-permanent interconnection area. In particular the layers in the permanent interconnection area preferably separable only at a higher separation force than the layers in the non-permanent interconnection area. The first compartment and the second compartment may for example each be partly surrounded by the permanent interconnection area and partly by the non-permanent interconnection area. Upon pressurizing the first component and/or second component the layers in the non-permanent interconnection may separate but the layers in the permanent interconnection may substantially not separate.

In one embodiment the device is adapted such that squeezing out the first component from the first compartment by compressing the first compartment causes the following sequence of steps:

the first component is preferably forced between the layers in the non-permanent sealing area between the first compartment and the second compartment;

the layers in the non-permanent sealing area preferably successively separate from each other in a direction toward the second compartment and thus enable the first component to advance between the separated layers toward the second compartment;

once the layers are separated along the entire distance between the first compartment and the second compartment preferably the separated layers form a passageway between the first compartment and the second compartment, wherein the passageway is laterally sealed by the permanent interconnection area;

the first component is preferably forced into the second compartment and thereby joins and pressurizes the second component;

at least one of the first component and the second component is preferably forced between the layers in the non-permanent sealing area between the second compartment and the reservoir;

the layers in the non-permanent sealing area preferably successively separate from each other in a direction toward the reservoir and thus enable at least one of the first component and the second component to advance between the separated layers toward the reservoir;

once the layers are separated along the entire distance between the second compartment and the reservoir preferably the separated layers form a further passageway between the second compartment and the reservoir, wherein this further passageway is laterally sealed by the permanent interconnection area;

the second and at least a portion of the first component preferably flow into the reservoir.

In one embodiment the sheet-like layers are two separate layers each having major inner and outer surfaces. The layers are preferably interconnected at their inner surfaces. The inner surfaces of the layers may be formed of a heat sealable plastic material, for example a polyethylene or polypropylene. One or both of the layers may comprise several interconnected sub-layers. For example one or both of the layers may comprise a metal sub-layer. Such a metal sub-layer may hinder the components stored within the device to permeate through the layer(s). One or both of the layers may further have one or more sub-layers of plastic material. Such a plastic sub-layer may exhibit superior barrier properties and thus may be used instead of a metal sub-layer. However such plastic layer may exhibit another property, for example a particular resistance to a certain chemical substance, good performance in heat sealing and/or good adhesion characteristics. The skilled person will recognize that instead of two separate layers a single layer folded to provide two portions may be likewise used for interconnection and forming the device according to the invention. Generally the layer(s) may have a thickness of between about 50 µm and about 500 µm, for example about 140 µm. The sub-layers may have a thickness of between about 5 µm and about 100 µm.

In a further embodiment one or both of the layers may comprise one or more bulges. For example one layer may have a bulge for providing the first compartment with a predetermined capacity, and a further bulge for providing the second compartment with a further predetermined capacity. This layer may further have a bulge for providing the reservoir with a predetermined capacity. Alternatively the other layer may have a bulge for providing the reservoir with a predetermined capacity. Accordingly one of the layers may comprise a bulge for each of the first compartment, the second compartment and the reservoir, or alternatively, one of the layers may comprise a bulge for each of the first compartment and the second compartment and the other layer may comprise a bulge for the reservoir. In these embodiments each of the layers may have a bulge for the first compartment, the second compartment and/or the reservoir. This means that a compartment may be formed by two bulges in combination or by one bulge in combination with a flat layer portion.

The device may for example have a bottom layer and a top layer. In use of the device for activation the device may be placed with the bottom layer on a flat surface, for example on a table top, so that the top layer faces away from that flat surface. Accordingly the top layer may comprise bulges for the compartments and the bottom layer maybe generally flat in an area opposite of the bulges. Further the bottom layer may comprise a bulge for the reservoir. A user may compress the first compartment by pressurizing and deforming the bulge toward the bottom layer. Thereby the device may be activated and at least part of the components may flow into the reservoir.

In a further embodiment the bottom layer and the top layer may have a bulge for forming the second compartment, whereas the first compartment may be formed by a flat portion of the bottom layer and a bulge in the top layer. Thus the first compartment may be arranged with the flat layer facing a flat surface for pressurizing the first compartment. The two bulges for the second compartment may provide the second compartment with a lower expandability relative to a compartment formed of a flat layer portion and a bulge. Thus the yielding or elasticity of the second compartment may be minimized so that forcing the first component into the second compartment may cause an essentially immediate opening of the second seal rather than the second compartment absorbs much of the first component. Accordingly the activation of the device may be facilitated.

In a further embodiment the first chamber and the second chamber are spaced apart at a distance of between about 1 mm to about 2 mm. Further the second chamber and the reservoir may be spaced apart at a distance of between about 1 mm to about 2 mm. Thus the non-permanent sealing areas or the seals between the first compartment and the second compartment or the second compartment and the reservoir may be minimized in length. This may help minimizing yielding of the overall volume formed by the compartments and the open seals. Consequently the precision of the mixing ratio may be maximized.

In one embodiment the top layer may be at least partially removable from the bottom layer to open the reservoir. For example the interconnection of the top and bottom layers around the reservoir may be non-permanent so that the layers can be manually peeled away from each other. Further the top layer may comprise a weakened line along which the bottom layer may be torn open, or the top layer may have an opening. The opening may be initially closed by a label which may be removed prior to use. The skilled person will recognize a variety of possibilities for providing an openable closure for the reservoir. In particular the opening or possibility to open may be provided at the top layer as mentioned or likewise in the bottom layer, for example in case the bulge for the reservoir is arranged in the top layer. An open or openable reservoir may provide a user visibility of the mixing quality of the first component and the second component in the reservoir. Further the open reservoir may facilitate rewetting of an instrument or brush used with the device.

In one embodiment the first compartment has a first capacity for the first component which is greater than a second capacity for the second compartment. In particular the first capacity may be greater than 1.5 of the second capacity, and in more particular the first capacity and the second capacity form a ratio of one of 2:1, 3:1, 4:1, 5:1 and 10:1 or 11:1. Accordingly the first compartment may contain a first amount of the first component which is greater than a second amount of the second component. In particular the first amount of the first component may be greater than 1.5 of the second amount of the second component, and in more particular the first amount of the first component and second amount of the second component form a ratio of one of 2:1, 3:1, 4:1, 5:1 and 10:1 or 11:1. The first amount may be about 140 µl and the second amount may be about 30 µl, for example. The greater capacity of the first compartment or the greater amount of the first component may allow for displacing substantially all of the second component from the second compartment by only compressing the first compartment. Therefore a predetermined mixing ratio between the first component and the second component may be achieved by the device.

In one embodiment the first amount of the first component substantially corresponds to the first capacity of the first compartment. Further the second amount of the second component may substantially correspond to the second capacity of the second compartment. Accordingly the first and/or the second compartments may be substantially air free filled in the respective first and/or second compartment(s). This may be achieved by filling the bulge for the respective compartment in the top layer substantially full before connecting the bottom layer onto the top layer.

In a further embodiment the dental material has a predetermined desired mixing ratio of the first component and the second component, and the device contains a first amount of the first component and a second amount of the second component at a ratio of the first amount and the second amount relative to each other which is different from the desired mixing ratio. In particular the desired mixing ratio may be defined by a quantity n of the first component relative to a quantity m of the second component, and the first amount of the first component present in the first compartment preferably corresponds to a quantity of about n+m and the second amount of the second component present in the second compartment preferably corresponds to a quantity of about m. Accordingly the amounts filled in the device preferably have a ratio of (n+m):m and because a portion m of the first amount of the first component preferably remains in the second compartment after activation of the device the resulting mixing ratio received in the reservoir is preferably (n+m−m):m or n:m.

Depending on the extent of the compression of the first compartment a percentage of x % of the first amount of the first component may remain in the first compartment. To account for such residual percentage of the first component and to achieve a final ratio of n:m in the reservoir the amounts filled in the device preferably have a ratio of (m+n)/(1−x %):m. Assuming that a portion of x % of the first component stays in the first compartment and a portion m stays in the second compartment the resulting mixing ratio received in the reservoir may be ((1−x %)*(m+n)/(1−x %)−m):m or (m+n−m):m or n:m.

In one embodiment the first compartment and the second compartment are arranged within an area in a plane of the layers that matches within a circle of about 20 mm. Thus the first compartment may be compressed using a thumb or finger and the second compartment may be compressed by rolling the thumb or finger toward the second compartment. Accordingly the same device may provide for dispensing two different predetermined mixing ratios (n:m and (n+m):m). The device may be placed on a generally flat surface for activating. Alternatively the first compartment and optionally the second compartment may be compressed between the thumb and a finger.

In a further embodiment the first compartment in a plane of the layers has an elliptical shape, and the second compartment is arranged in a dimension along the shorter axis of the ellipse. Thus the capacity of the first compartment may be maximized without substantially extending the size of first compartment in the dimension in which the thumb or finger can be rolled for compressing both compartments. Further the second compartment in a plane of the layers may have a circular or an elliptical shape. In case the second compartment has an elliptical shape the second compartment may be arranged such that the longer axis of the ellipse of the second compartment is oriented generally in line with the shorter axis of the ellipse of the first compartment. This may allow the first component to essentially entirely flush the second compartment in the direction of the liquid flow without leaving residual amount of the second component in areas of the second compartment. Further the skilled person will recognize other shapes providing similarly extension of capacity, although an elliptical shape with the long axis of the second compartment oriented in direction of the short axis of the first compartment may allow for minimized residual amounts of components. The ellipse of the first compartment may have a size in a dimension of the longer axis of about 16 mm and a size of about 10 mm in a dimension of the shorter axis, for example. The ellipse or circle of the second compartment may have a size in a dimension of one axis of about 6 mm to about 7 mm and may be smaller in the in a dimension perpendicular thereto.

In one embodiment the outlet is formed by an elongated channel which is formed by the layers. The channel may be adapted to receive an applicator for the dental material. For example the channel may be sized and shaped to retain an applicator therein. In particular the outlet may narrow from the reservoir toward an outside of the device, for example may have a constriction adjacent the outlet for engaging a groove in the applicator. The device may further comprise the applicator, for example a brush-like applicator. The device may have the applicator placed within the channel so that the reservoir is closed. This may prevent the reservoir to be contaminated, for example during shipment of the device.

In one embodiment the device comprises an encoding formed by shape of at least one of the layers. The encoding may be provided by embossing, punching or deep-drawing of one or both of the layers. The layers may for example be interconnected with each other by heat sealing and a tool for heat sealing may comprise the negative shape of the encoding. During heat sealing the tool may press the layer onto each other and thereby the encoding may be replicated onto the layer(s). This may allow for minimizing efforts for encoding the device, for example may allow for eliminating any printing.

In a further aspect the invention relates to a method of dispensing a dental material. The method comprises the steps of:
  providing a device according to the invention;
  compressing the first compartment and essentially not compressing the second compartment such that essentially all of the first component is displaced from the first compartment and at least part of the second component is displaced by the first component from the second compartment; and
  mixing at least portions of the first component and the second component in the reservoir.

In one embodiment the method further comprises the step of compressing the first compartment on a generally flat surface by use of a thumb or finger, and the step of rolling the thumb or finger towards the second compartment to compress the second compartment. Thus the device may be relative easy to use. Further the device may not be bent after compressing the first compartment as it may be practiced with other devices according to the background art to prevent the first and/or second components from flowing back toward the first component. The method may further comprise the steps of removing an applicator (for example a brush) from the channel, and agitating the components received in the reservoir by use of an applicator. The method may further comprise the step of rewetting the applicator by pushing the applicator through one of the layers into the reservoir. Thereby the layer may have an opening through which the applicator can be pushed, or the layer may be closed so that the layer opens as a consequence of pushing the applicator through the layer. The layer may have a predetermined weakened area for pushing the applicator through.

DETAILED DESCRIPTION OF THE INVENTION

Figure 1A:
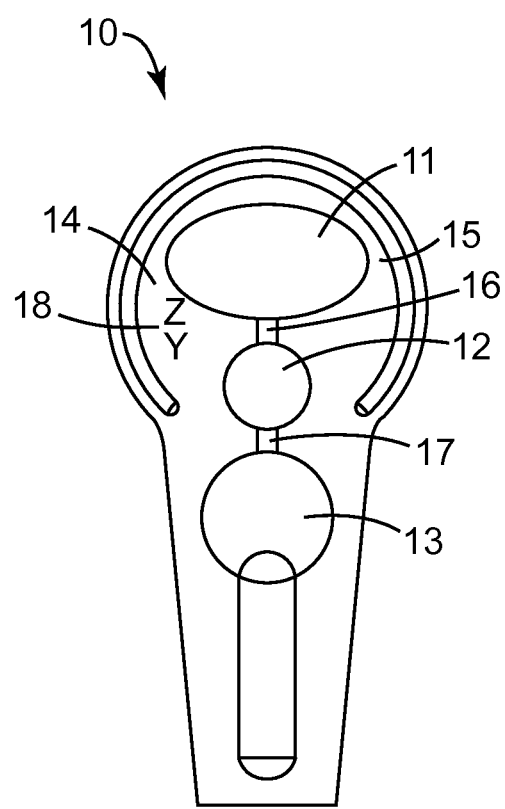
FIGS. 1A, 1B show a top and side view, respectively, of the device according to the invention.
Figure 1B:
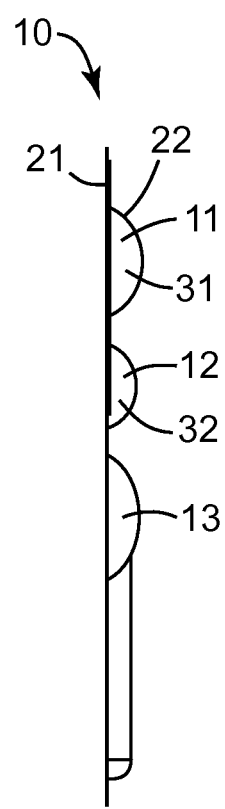

FIG. 1A shows a top view and FIG. 1B shows a cross-sectional side view of a device 10. The device 10 has a first compartment 11, a second compartment 12 and a reservoir 13.

The compartments 11, 12 are formed between a bottom layer 21 and a top layer 22. The layers 21, 22 are interconnected with each other to encapsulate a first component 31 within the first compartment 11 and a second component 32 in the second compartment 12. In particular the layers 21, 22 in the example are interconnected in a major interconnection area 14 around other areas in which an interconnection is suspended. For example the first compartment 11 and the second compartment 12 each are formed between non-interconnected areas of the layers 21, 22 and the interconnection area 14 entirely surrounds and thus seals such non-interconnected areas. Further the interconnection area 14 comprises a permanent interconnection area 15 and first non-permanent interconnection area 16 and second non-permanent interconnection area 17. The layers 21, 22 in the first non-permanent interconnection area 16 and the second non-permanent interconnection areas 17 form a first openable seal and a second openable seal for the compartments 11, 12, respectively. The first seal and the second seal may be opened by causing the layers 21, 22 to separate from each other in the non-permanent interconnection area, for example as a consequence of forcing the first and/or second component(s) between the layers 21, 22. The first non-permanent interconnection area 16 extends between the first compartment 11 and the second compartment 12, and the second non-permanent interconnection area 17 extends between the second compartment 12 and the reservoir 13. Accordingly at an inactivated stage of the device 10 in which the non-permanent interconnection areas 16, 17 are interconnected the first component 31 and the second component 32 are sealed within the respective first compartment 11 and the second compartment 12. Further at an activated stage of the device in which the non-permanent interconnection areas 16, 17 are separated the first compartment 11 and the second compartment 12 as well as the second compartment and the reservoir 13 are in fluid communication with one another.

The interconnection of the layers 21, 22 (in the inactivated stage of the device 10) in the non-permanent interconnection areas 16, 17 is preferably of a lower bond strength than the permanent interconnection of the layers 21, 22 in the permanent interconnection area 15. The interconnection between the layers may be formed, for example by adhesive bond or fusion of the layers with each other. For example the layers may generally be interconnected by heat sealing. Different bond strengths for the interconnection between the layers may be achieved by using different temperatures and/or different sealing durations.

The device 10 may be activated by compressing the first compartment 11 so that the first component 31 is pressurized and causes the first seal formed by the first non-permanent interconnection area 16 to open.

The second compartment 12 is dimensioned smaller in capacity than the capacity needed to contain the second component 32 and additionally the first component 31. Thus once a fluid communication is established between the first compartment 11 and the second compartment 12 a further compression of the first compartment 11 preferably also causes the second seal formed by the second non-permanent interconnection area 17 to open. Accordingly squeezing out the first component 31 from the first compartment 11 by compressing the first compartment 11 causes the first seal and the second seal to open. This may help for minimizing the efforts for activation of the device, for example preferably allows for activating the device by only compressing the first compartment 11 without compressing the second compartment 12.

Preferably the openable seals are adapted to open due to pressurizing the first component by applying finger pressure to the first compartment. Finger pressure is preferably in a range of about 5 N to about 70 N, preferably in a range of about 15 N to about 50 N.

The device 10, as illustrated in the cross-sectional side view, may comprise a larger top layer 22 and a larger bottom layer 21 forming both compartments 11, 12. However, a larger bottom layer may also be used in combination with individual top layers for forming the compartments 11, 12. Alternatively a larger top layer may be used in combination with individual bottom layers to form the compartments 11, 12. In another alternative embodiment the compartments 11, 12 may also each be formed individually by separate top and bottom layers, and the partial devices so formed may be interconnected to form the device according to the invention.

The layers may be bulged out to provide a certain predetermined capacity of the compartments 11, 12, as shown at top layer 22 in FIG. 1B. Such bulges further may facilitate filling. For example, the bulges of layer 22 may be filled with components prior to interconnecting the layer 22 with the bottom layer 21. The bulges may in addition or instead be arranged in bottom layer 21. The terms "top" and "bottom" for the purpose of this specification designate the arrangement of the layers during a preferred use of the device, for example with the device placed with the bottom layer on a table top so that the top layer is oriented to a user. The skilled person will however recognize that the selected designation of the layers does not limit the orientation at which the device may be used.

The compartments of the device may have a capacity to store quantities of between about 0.01 ml and about 3 ml. Therefore the device may be suitable for providing material in the rather small quantities typically used in dentistry. Preferably the individual compartments of the device have a capacity to provide a total quantity of material sufficient for a single dental treatment. Such total quantity may be between about 0.03 ml and about 1.5 ml. The mixing ratio may for example be 2:1, 3:1 or 4:1 for example, but may generally be selected at values between, or outside as appropriate.

The device 10 further comprises an encoding 18. In the example the top layer 22 has embossed indicia "ZY". Such indicia may provide any information as desired, in particular the product name or type contained in the device, a brand name, a company name, a date of manufacturing, or an expiry date, for example. Such an embossing may be advantageous in that it may be provided automatically along with sealing of the layers 21, 22. For example a tool used for pressurizing the layers 21, 22 onto each other may have a recessed structure having the negative shape of the indicia so that pressurizing the layers provides an impression or embossing of that structure in at least the layer facing the tool. The tool may further comprise a punch for punching the indicia into the layer or layers.

The invention claimed is:

1. A device for dispensing a dental material, comprising:
  a first and a second compartment formed between interconnected sheet-like layers, the first compartment at an inactivated stage encapsulating a first flowable component of the dental material;
  the second compartment at an inactivated stage encapsulating a second flowable component of the dental material, wherein the first compartment and the second compartment are substantially air free at an inactivated stage;
  a reservoir for jointly holding at least parts of the first component and the second component at an activated stage;
  a first seal openably sealing the first compartment and the second compartment at the inactivated stage from each other;
  a second seal openably sealing the second compartment and the reservoir at the inactivated stage from each other;
  each of the first seal and the second seal being formed by the layers in a non-permanent sealing area in which the layers are interconnected such that they are disconnectable in consequence of forcing a component of the dental material between the layers;
  wherein the capacity of the first compartment and the second compartment relative to each other is dimensioned such that squeezing out the first component from the first compartment by compressing the first compartment causes the first seal and the second seal to open; and
  wherein, when the device is in the activated stage, the dental material has a predetermined desired mixing ratio of the first component and the second component, and, when the device is in the inactivated stage, the device contains a first amount of the first component in the first compartment and a second amount of the second component in the second compartment at a ratio of the amounts which is different from the desired mixing ratio;
  wherein the desired mixing ratio is defined by a quantity n of the first component relative to a quantity m of the second component, and wherein the first amount of the first component present in the first compartment corresponds to a quantity of about n+m and the second amount of the second component present in the second compartment corresponds to a quantity of about m.

2. The device of claim 1, wherein at least one of the layers has a bulge for providing the first compartment with a predetermined capacity, and a further bulge for providing the second compartment with a further predetermined capacity.

3. The device of claim 1, wherein the first compartment has a first capacity for the first component which is greater than a second capacity for the second compartment.

4. The device of claim 3, wherein the first capacity is greater than twice of the second capacity.

5. The device of claim 4, wherein the first capacity and the second capacity form a ratio of one of 3:1, 4:1, 5:1, 10:1 or 11:1.

6. The device of claim 1, wherein the first compartment and the second compartment are arranged within an area in a plane of the layers that matches within a circle of about 20 mm.

7. The device of claim 6, wherein the first compartment in a plane of the layers has an elliptical shape with a longer axis and a shorter axis, and wherein the second compartment is arranged in a dimension along the shorter axis of the ellipse.

8. The device of claim 7, wherein the second compartment in a plane of the layers has an elliptical shape with a longer axis and a shorter axis, with the longer axis of the ellipse of the second compartment being oriented generally in line with the shorter axis of the ellipse of the first compartment.

9. The device of claim 1, wherein the outlet is formed by an elongated channel which is formed by the layers, and wherein the channel is adapted to receive an applicator for the dental material.

10. The device of claim 1, comprising an encoding formed by a shape formed in at least one of the layers.

11. The device of claim 1, wherein, when the device is in the activated stage, the device has a dispensed amount of dental material substantially equal to the amount of the first component in the first compartment when the device is in the inactivated stage.

12. The device of claim 1, wherein, when the device is in the activated stage, a predetermined portion of the first component is present in the second compartment.

13. A method of dispensing a dental material comprising the steps of:
providing a device as claimed in claim 1;
compressing the first compartment and essentially not compressing the second compartment such that essentially all of the first component is displaced from the first compartment and at least part of the second component is displaced by the first component from the second compartment; and
mixing at least portions of the first component and the second component in the reservoir.

14. The method of claim 13, further comprising the step of compressing the first compartment on a generally flat surface by use of a thumb or finger, and the step of rolling the thumb or finger towards the second compartment to compress the second compartment.

15. A device for dispensing a dental material, comprising:
a first and a second compartment formed between interconnected sheet-like layers, the first compartment at an inactivated stage encapsulating a first flowable component of the dental material;
the second compartment at an inactivated stage encapsulating a second flowable component of the dental material, wherein the first compartment and the second compartment are substantially air free at an inactivated stage;
a reservoir for jointly holding at least parts of the first component and the second component at an activated stage;
a first seal openably sealing the first compartment and the second compartment at the inactivated stage from each other;
a second seal openably sealing the second compartment and the reservoir at the inactivated stage from each other;
each of the first seal and the second seal being formed by the layers in a non-permanent sealing area in which the layers are interconnected such that they are disconnectable in consequence of forcing a component of the dental material between the layers;
wherein the capacity of the first compartment and the second compartment relative to each other is dimensioned such that squeezing out the first component from the first compartment by compressing the first compartment causes the first seal and the second seal to open; and
wherein, when the device is in the inactivated stage, the device contains a first amount of the first component in the first compartment and a second amount of the second component in the second compartment at a first ratio, and when the device is in the activated stage, the dental material has an activated mixing ratio of the first component and the second component that is different from the first ratio;
wherein the activated mixing ratio is defined by a quantity n of the first component relative to a quantity m of the second component, and wherein the first amount of the first component present in the first compartment corresponds to a quantity of about n+m and the second amount of the second component present in the second compartment corresponds to a quantity of about m.

* * * * *